(12) United States Patent
Lobb et al.

(10) Patent No.: US 7,584,521 B2
(45) Date of Patent: Sep. 8, 2009

(54) DUST MITIGATION AND SURFACE CLEANING SYSTEM FOR MAINTAINING A SURFACE FREE FROM DUST AND OTHER MATERIALS

(75) Inventors: Clarence T. Lobb, Albuquerque, NM (US); William T. Kornke, Rio Rancho, NM (US); Wayne T. Armstrong, Placitas, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 537 days.

(21) Appl. No.: 11/312,489

(22) Filed: Dec. 21, 2005

(65) Prior Publication Data
US 2007/0136978 A1   Jun. 21, 2007

(51) Int. Cl.
*F23J 3/02* (2006.01)
(52) U.S. Cl. ...................... 15/316.1; 15/320
(58) Field of Classification Search ............... 15/300.1, 15/320, 322, 340.1, 340.2, 339, 328, 316.1; 134/94.1, 95.1, 95.2, 99.1, 102.1, 102.2, 134/37
See application file for complete search history.

(56) References Cited

U.S. PATENT DOCUMENTS

| | | | | |
|---|---|---|---|---|
| 4,411,675 | A | * | 10/1983 | de Castella ................. 96/140 |
| 5,399,319 | A | | 3/1995 | Schoenberger et al. |
| 5,657,929 | A | | 8/1997 | DeWitt et al. |
| 6,750,467 | B2 | | 6/2004 | Tulip |
| 6,944,908 | B2 | | 9/2005 | Hoetzer et al. |

* cited by examiner

*Primary Examiner*—Dung Van Nguyen
(74) *Attorney, Agent, or Firm*—Edell, Shapiro & Finnan, LLC

(57) ABSTRACT

A dust mitigation and cleaning system for cleaning a surface includes a system housing secured around at least a portion of a section including the surface to be cleaned. The system housing includes a hollow member extending within the system housing toward and in general alignment with the surface to be cleaned, where an outlet of the system housing is defined by the hollow member. A duct section is secured to a portion of the system housing and includes an inlet to receive a gaseous fluid, such as air from an ambient environment in which the system is disposed, and an outlet in communication with the system housing. The system further includes a pressure generator disposed within the duct section, where operation of the fan generates a pressure differential between an interior portion of the system housing and the ambient environment such that gaseous fluid drawn into the system housing via the duct section is removed from the interior portion of the system housing via the outlet defined by the hollow member. In an exemplary embodiment, the system is disposed within a motorized vehicle to maintain a sensor window used with optical equipment clean during system operations.

28 Claims, 7 Drawing Sheets

DUST MITIGATION AND SURFACE CLEANING SYSTEM FOR MAINTAINING A SURFACE FREE FROM DUST AND OTHER MATERIALS

GOVERNMENT INTERESTS

This invention was made with U.S. Government support and the U.S. Government may have certain rights in the invention as provided for by the terms of contract No. W911SR-05-C-0015.

BACKGROUND OF THE INVENTION

1. Field of the Invention

The present invention relates to systems and corresponding methods for mitigating dust and maintaining windows and other surfaces clean.

2. Description of the Related Art

The monitoring of air quality and, in particular, toxic and hazardous compositions within certain ambient (e.g., outdoor) environments is important in certain applications, such as in combat or other military operations or at large industrial complexes (e.g., chemical production facilities). Spectroscopy (e.g., infrared or Raman spectroscopy) is a highly useful technique in monitoring air quality by identifying components and determining their compositions within the air at one or more designated locations.

For example, certain spectroscopic equipment, including one or more optical sensors (e.g., lasers) and/or detectors, can be provided within a motorized vehicle to facilitate monitoring of the air quality at selected areas of the surrounding environment as the vehicle traverses a field or other terrain. The equipment is maintained within a secured housing within the vehicle to prevent dust and other materials from coming into contact with and potentially damaging the equipment. In addition, a portal or window is provided at a suitable location with respect to the equipment housing and vehicle to facilitate transmission and/or detection of an optical signal between the sensor within the housing and the ground or some other surface to be monitored outside the vehicle.

When using such equipment, it is important to maintain the sensor window as clean as possible. However, this can become very difficult in certain environments, such as environments that can become dust-laden (e.g., deserts) and/or muddy (e.g., swamps).

OBJECTS AND SUMMARY OF THE INVENTION

In light of the above, and for other reasons that become apparent when the invention is described, an object of the present invention is to provide a system that maintains a window clean and free from dust, mud or other materials to which the window may be exposed.

Another object of the present invention is to provide a system for maintaining a sensor window of an air quality monitoring system in an outdoor environment free from dust or other materials.

The aforesaid objects are achieved individually and in combination, and it is not intended that the present invention be construed as requiring two or more of the objects to be combined unless expressly required by the claims attached hereto.

In accordance with the present invention, a dust mitigation and cleaning system for cleaning a surface includes a system housing secured around at least a portion of a section including the surface to be cleaned. The system housing includes a hollow member extending within the system housing toward and in general alignment with the surface to be cleaned, where an outlet of the system housing is defined by the hollow member. A duct section is secured to a portion of the system housing and includes an inlet to receive a gaseous fluid (e.g., air) from a selected environment (e.g., an ambient environment in which the system is disposed) and an outlet in communication with the system housing. The system further includes a differential pressure generator (e.g., a fan, a pump or compressor, etc.) disposed within the duct section, where operation of the pressure generator generates a pressure differential between an interior portion of the system housing and the ambient environment such that gaseous fluid drawn into the system housing via the duct section is removed from the interior portion of the system housing via the outlet defined by the hollow member.

Preferably, the system is secured or mounted to a motorized vehicle, the system housing is configured to be secured around at least a portion of a housing structure that contains optical sensor equipment, and the surface to be cleaned comprises a sensor window defining a wall portion of the housing structure.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION OF THE PREFERRED EMBODIMENTS

In accordance with the present invention, a dust mitigation and surface cleaning system is configured to provide a supply of forced air or other fluid (e.g., nitrogen) against a surface, such as a window, to remove and/or minimize contact of dust, mud and other materials with respect to the surface. Alternatively, or in combination with the forced fluid supply, the system can include another fluid supply source and one or more spray nozzles to direct a flow of fluid toward the surface in any one or more selected spray patterns to remove materials from the surface.

The dust mitigation and surface cleaning system is described herein for use with an outside air quality monitoring and detection system that is mounted within a motorized vehicle, where the system maintains a sensor window substantially clean in order to facilitate suitable detection and concentration measurements of certain components within the ambient air environment surrounding the vehicle. However, it is noted that the dust mitigation and surface cleaning system can be implemented for use in maintaining a clean surface for indoor or outdoor applications, particularly where it is desirable to maintain the surface substantially free from dust and/or other materials.

Figure 1:
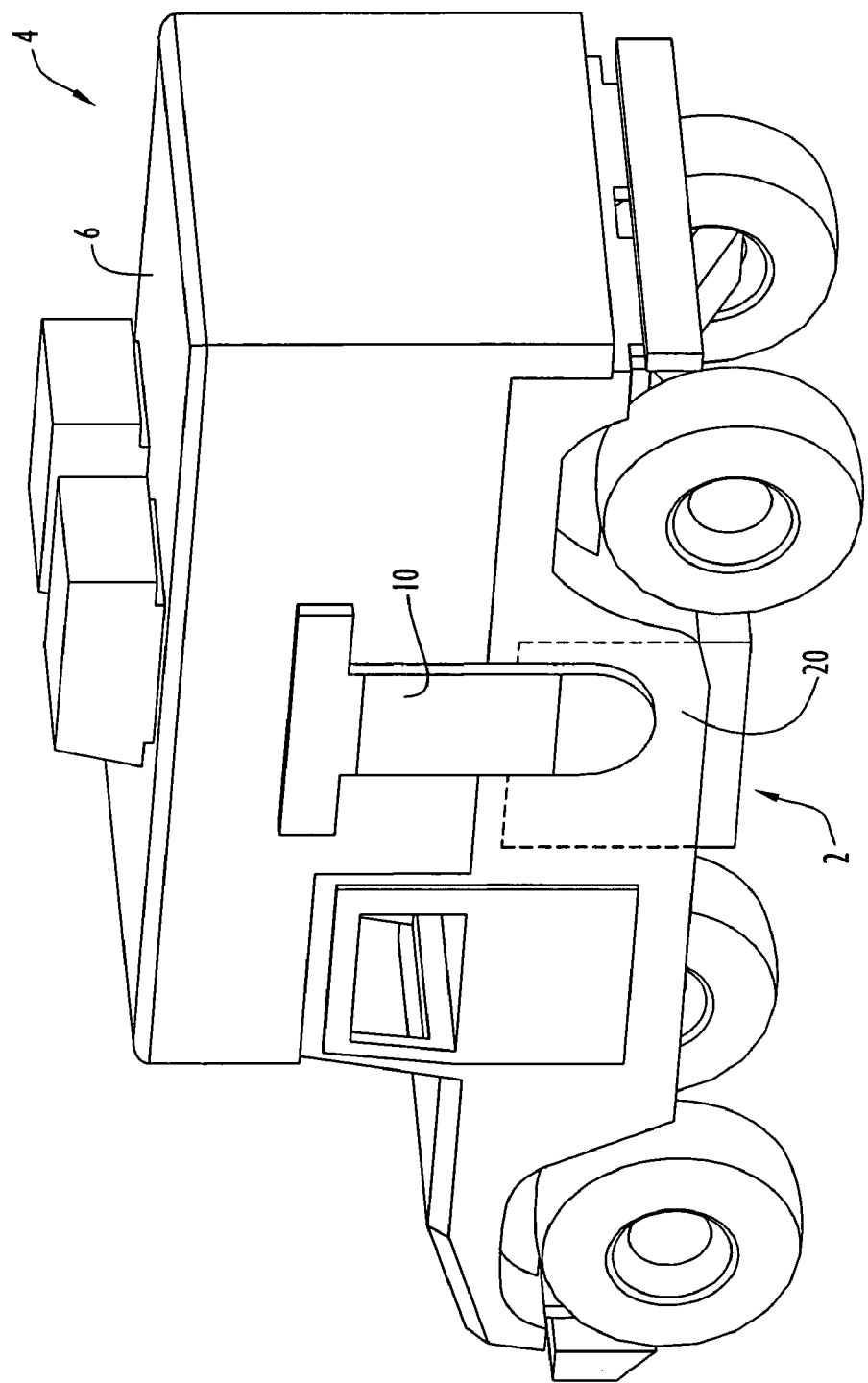
FIG. 1 is a view in perspective of a vehicle that includes an air quality monitoring system used in combination with a dust mitigation and surface cleaning system in accordance with the present invention.

Referring to FIG. 1, a dust mitigation and surface cleaning system 2 is implemented for use in a motorized vehicle 4 (e.g., an all-terrain vehicle such as a High Mobility Multipurpose Vehicle or Hum-Vee). Vehicle 4 includes a compartment 6 that serves as a shelter for the air quality monitoring and detection system as well as operators of the system. The air quality monitoring and detection system includes sensor equipment that is used to monitor air quality and identify and determine the composition of certain components in the air. In an exemplary embodiment, the sensor equipment includes a laser to transmit a laser signal toward and a detector to measure a reflected signal from a ground surface in order to facilitate spectroscopic measurements of the surrounding environment using Raman scattering or some other suitable technique. An optical signal is directed from the sensor equipment within compartment 6 and along an optical path that is defined through the vehicle as described below, and toward the ground surface beneath the vehicle. The sensor equipment can be designed to conduct an air quality measurement by scanning with the optical signal at any suitable rate (e.g., about 25 or more scans per second).

As can be seen from FIG. 1, dust mitigation and surface cleaning system 2 is mounted along one side of the vehicle and at a location proximate and just to the front of one of the rear tires. The system includes a duct section 10 that extends along an exterior side wall of the vehicle and also through a vehicle side wall portion to connect with a protective housing 20, referred to as a dog house, of system 2. The dog house as well as other components of the dust mitigation and surface cleaning system can be constructed of any suitable materials, such as metals (e.g., steel and/or aluminum) and/or plastics (e.g., polyolefins such as polyethylene).

Figure 2:
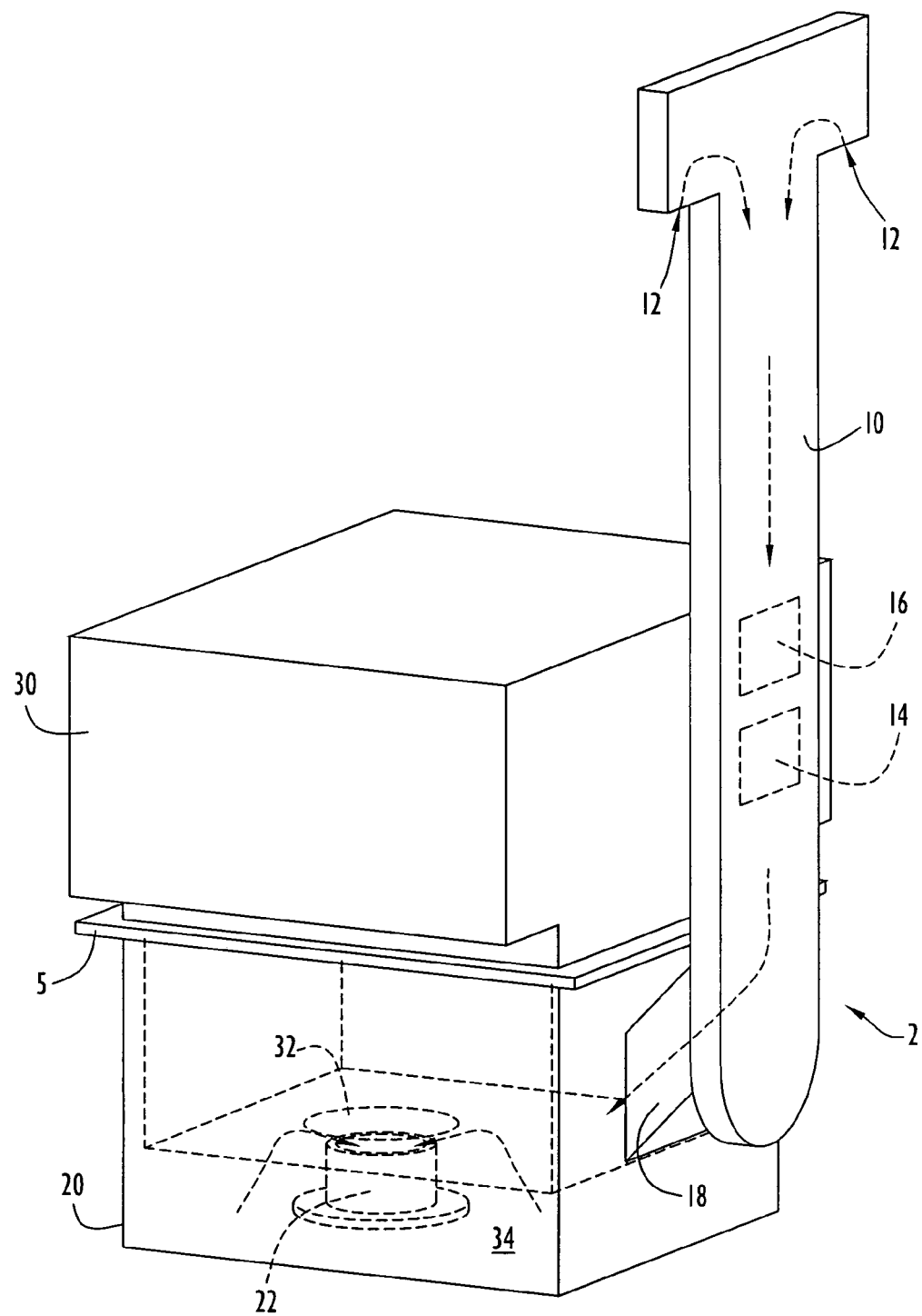
FIG. 2 is a view in perspective and partial section of the dust mitigation and surface cleaning system with the air quality monitoring system of FIG. 1.

As can best be seen from FIG. 2, dog house 20 connects to an underside and is supported by a lower surface portion 5 of the vehicle frame or chassis that also defines a lower support surface or floor of vehicle compartment 4. The dog house is preferably secured to lower surface portion 5 at a location where the vehicle chassis body is elevated with respect to other lower surface portions (e.g., at or near the wheel well of the vehicle chassis). This allows the dog house to be elevated as far as possible from the ground surface upon which the vehicle traverses.

A lower end of duct section 10 includes an outlet 18 that extends through a cut-out section of the vehicle side wall and within a side wall portion of dog house 20. An upper end of the duct section includes openings 12 that serve as inlets to the duct section for drawing air into the duct section and into the dog house as described below. A fan 14 is mounted within the duct section to draw the air from the inlet openings 12 into the dog house, and a filter 14 is also mounted within the duct section at a suitable location upstream from the fan to filter particulate materials of selected sizes (e.g., dust particles, sand, etc.) from the incoming air prior to delivery to the dog house. The filter can be of any suitable type, mesh or screen size and/or configuration to meet the specifications of a particular application (e.g., applications in which particulate material of a specified diameter or size must be removed from the incoming air prior to delivery of the air to the dog house).

The fan can be of any suitable size and/or type (e.g., fixed or variable speed) to control the flow of air at a selected flow rate and velocity for a particular application. For example, a suitable fan can be selected to draw air into the duct section at a velocity of about 10 mph (about 4.47 meters/second). The fan can be actuated via a power switch disposed at any suitable location on system 2 and/or within vehicle 4, such as in the cabin or driving compartment of the vehicle or, alternatively, within compartment 6, to allow the driver or operator to selectively control operation of the fan during operation of the sensor equipment. In addition, the fan can be powered by any suitable power supply source (e.g., the vehicle main battery, a specified battery for the system or other supply sources).

While a fan is shown in system 2, it is noted that any other suitable pressure differential device can be provided to draw air (or any other fluid) into the dog house. For example, a pump or compressor could be provide to generate a desired pressure differential that facilitates the flow of air into and through the dog house.

An equipment housing 30 is secured within vehicle compartment 6 and extends through a cut-out section or opening in lower surface portion 5 of the vehicle, such that a portion of the equipment housing extends within dog house 20 at a selected distance (e.g., about 4-5 inches or about 10-13 centimeters) from a lower wall portion of the dog house. A gap 34 within dog house 20 is defined as the space between the dog house and the portion of the equipment housing extending within the dog house. Outlet 18 of duct section 10 extends within dog house 20 so as to be generally aligned near or below a lower or bottom surface of equipment housing 30, such that air flowing from the duct section enters the gap in the dog house. In addition, the duct section outlet is oriented to generally direct air toward the lower or bottom surface of the dog house.

The equipment housing surrounds and protects the sensor equipment (e.g., laser, detector and related equipment) disposed within the housing. In addition, a lower wall portion of equipment housing 30 includes a cut-out section in which a transparent sensor window 32 is provided. The sensor window can be constructed of glass, plexi-glass or any other suitable transparent and sufficiently rigid material that facilitates transmission of an optical signal through the window. In addition, the sensor window can be of any suitable dimensions and geometric configurations (e.g., square, round, oval, etc.). For example, the sensor window can have a circular configuration (as depicted in FIGS. 1 and 2) with a diameter of about 6 inches (about 15 centimeters). However, depending upon a particular application, the sensor window can be of greater or smaller dimensions. The sensor window is tightly sealed with respect to the cut-out section of the equipment housing to prevent dust, air or any other material from entering the equipment housing at the sensor window during system operation.

The lower wall portion of dog house 20 includes a generally cylindrical, hollow and tubular member 22 that extends upward toward equipment housing 30 in alignment with sensor window 32. The tubular member further extends through the lower wall of the dog house to provide an opening from the dog house to the surrounding environment. Tubular member 22 extends a selected distance toward equipment housing 30 to leave a small gap between the end of member 22 and sensor window 32. For example, the system can be designed such that the distance between the tubular member and the window surface is no greater than about 2 inches (about 5 centimeters). The tubular member has dimensions that generally correspond with the dimensions of the sensor window. In an exemplary embodiment where the sensor window has a diameter of about 6 inches (about 15 centimeters), the inside diameter of the tubular member preferably has about the same dimension. While the tubular member depicted in FIG. 2 is cylindrical, the tubular member can have any cross-sectional geometric configuration (e.g., rectangular, oval, etc.). Thus, the dog house is open to the surrounding environment below the vehicle, and the sensor window and the tubular member are suitably aligned with each other to define a linear optical path for an optical signal to be transmitted (e.g., a laser beam from a laser) from within housing 30 toward a ground surface that supports and is traversed by the vehicle during a scanning operation.

In operation, vehicle 4 is driven along a selected terrain, while the sensor equipment within equipment housing 30 selectively scans the terrain by transmitting an optical signal (e.g., a laser beam from a laser) along the optical path, as defined by sensor window 32 and the opening provided by tubular member 22 of dog house 20, toward the ground surface beneath the vehicle. The signal reflected by the ground surface is also received by the sensor equipment via the optical path. The reflected signal is then analyzed to determine the presence and concentration of substances within the air and/or at the ground surface.

Depending upon a particular environment in which the vehicle is traveling, it is possible for dust, mud and/or other materials from the surrounding environment to enter through tubular member 22 and into gap 34 within the dog house and to potentially collect or accumulate on sensor window 32. System 2 effectively minimizes or removes such materials from gap 34 as well as any materials that may collect on the sensor window by actuation of fan 14 to draw air into duct section 10, via inlet openings 12, and into the gap of dog house 20. Air that is drawn into the duct section is processed by filter 16 to remove particulate material (e.g., dust) from the air stream prior to entering the dog house. The air stream is directed by duct section outlet 18 toward the lower or bottom surface of the dog house, where it is then circulated throughout gap 34 and toward sensor window 32.

The fan basically generates a pressure differential between the dog house and the ambient environment surrounding the dog house, where air flows into the dog house gap and ultimately passes out through tubular member 22 and back into the ambient environment (which is at a lower pressure than the pressure within gap 34). The air flowing within gap 34 entrains dust and/or any other materials that may have entered into the dog house gap, such that these materials flow with the air through tubular member 22 and out of the dog house back to the ambient environment. Since the entrance to the tubular member is proximate sensor window 32, the swirling air currents moving toward the tubular member tend to contact and remove any material that may have collected on the sensor window prior to leaving the dog house through tubular member 22. The swirling air currents also minimize or prevent contact between the sensor window and dust and/or any other materials that may be within the dog house by continuously wiping the sensor window. The continuous operation of the fan and the resultant forced air flow from the dog house further substantially limits or prevents any other dust and/or other foreign particles or materials in the ambient environment from entering the dog house.

Duct section fan 14 can be used continuously during operation of the sensor equipment, so as to minimize or prevent any dust or other materials from even entering into dog house 20. Alternatively, fan 14 can be selectively actuated by an operator (e.g., via a control switch as described above) during operation of the sensor equipment and during periods when the potential for entry of foreign materials within the dog house increases (e.g., during sand or dust storms in desert-like environments, during movement of the vehicle along muddy terrain, etc.).

Figure 3:
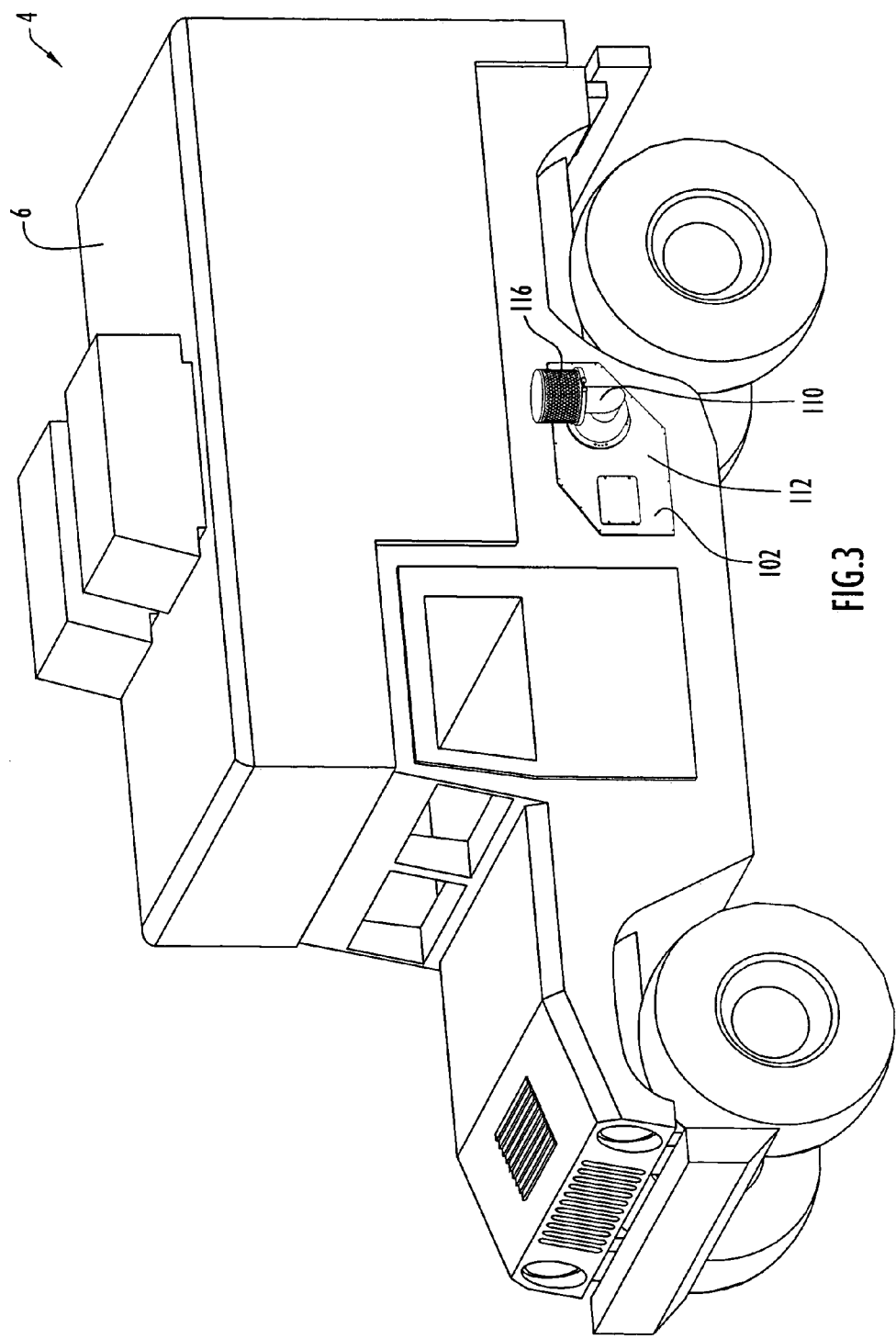
FIG. 3 is a view in perspective of a vehicle that includes an air quality monitoring system used in combination with a dust mitigation and surface cleaning system in accordance with an alternative embodiment of the present invention.
Figure 4:
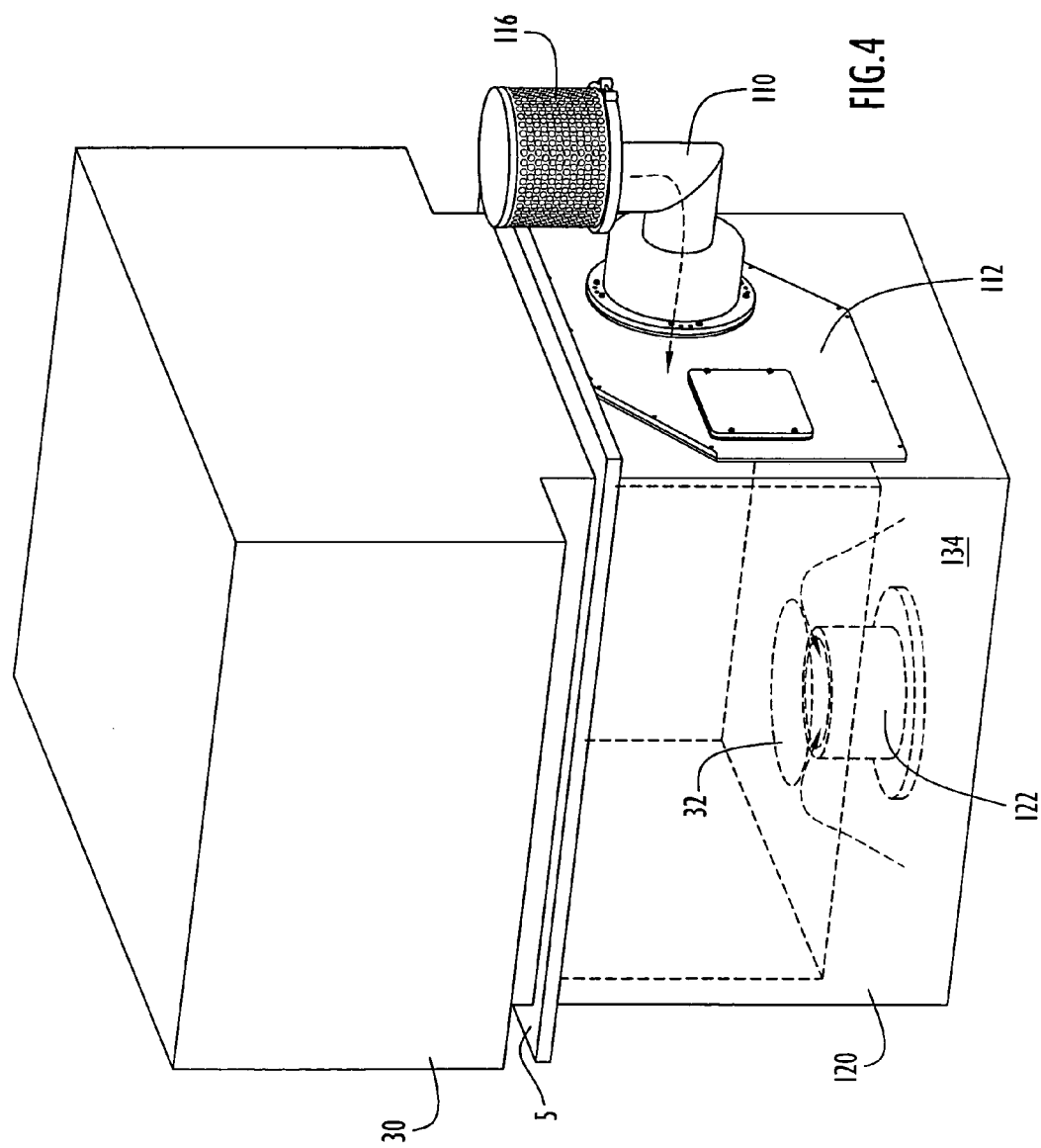
FIG. 4 is a view in perspective and partial section of the dust mitigation and surface cleaning system with the air quality monitoring system of FIG. 3.
Figure 5:
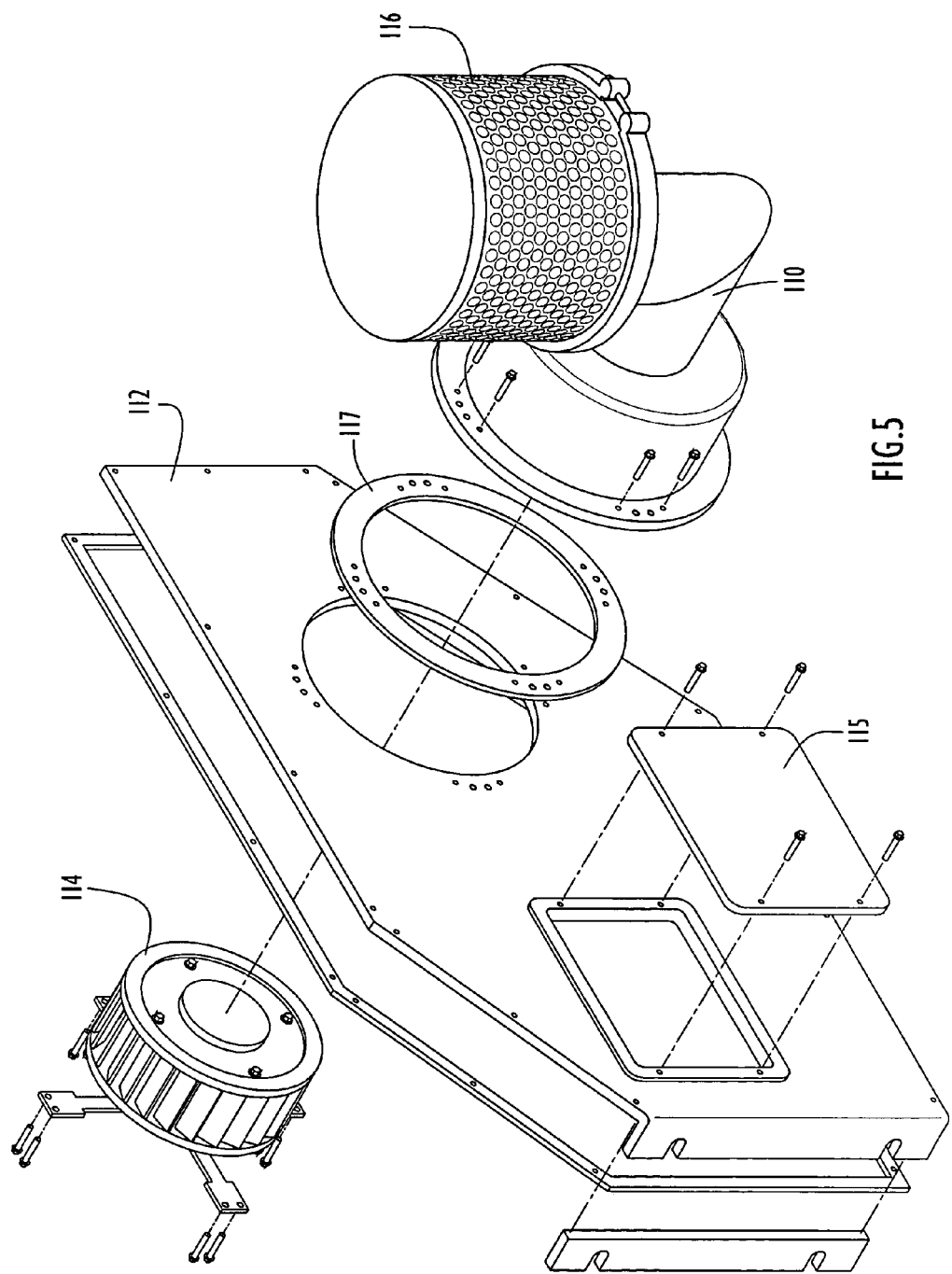
FIG. 5 is an exploded view of the duct section including fan and filter housing for the dust mitigation and surface cleaning system of FIG. 3.

An alternative embodiment of a dust mitigation and surface cleaning system is depicted in FIGS. 3-5. Referring to FIGS. 3 and 4, system 102 is similar in design as the system described above and depicted in FIGS. 1 and 2, where system 102 is mounted along vehicle 6 at a similar location (i.e., proximate and to the front of a rear tire of the vehicle). The system includes a dog house 120 that connects with an underside and is supported by lower surface portion 5 of the vehicle chassis or body that also defines a lower support surface or floor of vehicle compartment 4. Equipment housing 30, which contains sensor equipment of the types described above, is mounted within the vehicle compartment and extends through a cut-out section of lower surface portion 5 and into dog house 120. As in the previous embodiment, a gap 134 is defined as the space between the dog house and the portion of the equipment housing extending within the dog house, and a tubular member 122 extends from a cut-out section of a lower or bottom wall surface of the dog house and is aligned and proximate with a sensor window 32 formed in a lower or bottom surface of equipment housing 30 so as to define an optical path for transmission of an optical signal between the sensor equipment and the ground that is traversed by the vehicle.

Referring to FIG. 5, system 102 further includes a duct section 110 connecting with a side wall of the dog house and extending through an exterior side wall of vehicle 4. In particular, a duct section 110 is connected to a panel 112 (with a gasket 117 disposed between the duct section and panel to provide an airtight seal), and the panel secures to a cut-out section of a side wall portion of the vehicle body. A generally cylindrical filter housing 116 is secured at the inlet of the duct section. The filter housing includes a grill and contains a suitable filter to remove particulate material (e.g., dust) from the air being drawn within the duct section. Any suitable air filter (e.g., a conventional auto air filter) can be provided depending upon a particular application and the sizes and types of particulate material that need to be filtered. The location of filter housing 116 in system 102 facilitates easy removal and replacement of the filter.

A fan 114 is secured within a portion of duct section 110, and the fan can optionally include a power switch that can be mounted at any suitable location (e.g., in the vehicle cabin where the driver is seated or in compartment 6 so as to be accessibly by an operator of the sensor equipment). The fan can be powered by any suitable power supply source (e.g., the vehicle main battery or a specified battery for the system). An outlet of the duct section is provided at a suitable location within gap 134 of the dog house. A removable access panel 115 is also secured to main panel 112.

The dust mitigation and surface cleaning system operates in a substantially similar manner as the previous embodiment described above and depicted in FIGS. 1 and 2. In particular, air that is drawn in through duct section 110 is initially filtered as the air passes through filter housing 116. The air stream enters dog house gap 134, swirls around within the gap and then passes through tubular member 122. The airflow path is brought in close proximity and/or contact with sensor window 32 (due to the close spacing between the tubular member and the sensor window), and any dust and/or other material within the dog house gap or on the sensor window becomes entrained with the air and is removed through the tubular member.

Figure 6:
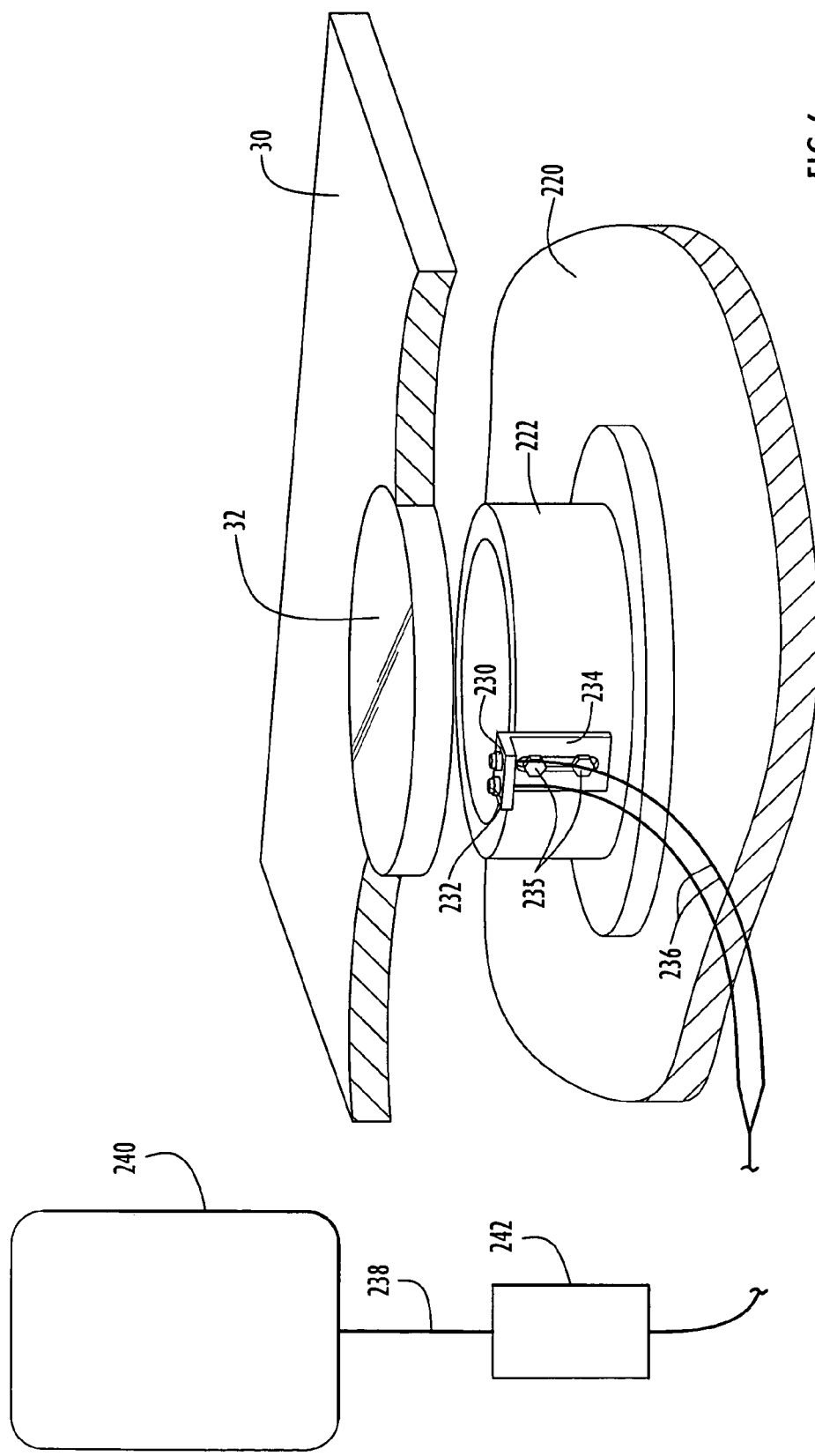
FIG. 6 is a view of a portion of a dust mitigation and surface cleaning system in accordance with another embodiment of the invention, in which the system includes spray nozzles for cleaning a sensor window of the air quality monitoring system.

While the systems described above are effective in minimizing or even preventing the presence of dust and/or other materials on the sensor window and also within the gap defined within the dog house, the systems can be further enhanced by providing a fluid spray device that directs fluid toward the sensor window to remove materials (e.g., mud) that may stick to the window. Referring to FIG. 6, a portion of a dog house 220 for a dust mitigation and surface cleaning system and also a portion of equipment housing 30 are depicted, where it is understood that the dog house and equipment housing are substantially similar in configuration and design as any of the previous embodiments. The equipment housing includes a sensor window 32, and the dog house includes a tubular member 222 that extends from a lower or bottom wall of the dog house to be closely spaced and aligned with the sensor window. As in the previous embodiments, the dust mitigation and surface cleaning system provides a flow of air at a suitable flow rate to remove or prevent the presence of dust and/or other materials both on the sensor window and within the dog house gap.

In addition, two spray nozzles 230 and 232 are secured to tubular member 222 via an adjustable bracket 234. In particular, the nozzles are secured at one end of the bracket, and the bracket includes an elongated groove in which fasteners 235 (e.g., threaded screws) are inserted to secure the bracket to the tubular member. The position of bracket 234 can be adjusted by fasteners 235 with respect to tubular member 222 so as to secure spray nozzles 230 and 232 at a variety of different distances with respect to sensor window 32. For example, the spray nozzles can be provided nearly flush with the upper surface of the tubular member so as to be within about 2 inches (about 5 centimeters) from the surface of the sensor window. The bracket can also be repositioned such that the spray nozzles are closer (e.g., less than 2 inches) to the sensor window. A fluid line 236 is connected with each spray nozzle, and the fluid lines combine to form a single or main fluid line 238 that extends to a reservoir 240 (e.g., a polyethylene tank). The reservoir can have be of any suitable size (e.g., a 0.5 gallon or 2 liter capacity tank) to store cleaning fluid and can further be mounted at any suitable location (e.g., within the dog house, within the vehicle compartment or at any other suitable location of the vehicle). The reservoir contains a suitable cleaning fluid (e.g., water, an alcohol, a suitable windshield cleaning fluid, and/or combinations thereof) that is dispersed to the spray nozzles at a selected pressure and flow rate via fluid lines 236, 238. A pump 242 is disposed along main fluid line 238 between the reservoir and the nozzles. The pump can be of any suitable type and configuration (e.g., a 24 Volt pump) to deliver the fluid at the desired pressure within the fluid lines. A power switch for the pump can be provided at any suitable location (e.g., in the vehicle cabin where near the vehicle driver, within compartment 6 near the sensor equipment, etc.) to facilitate selective spraying of fluid on the sensor window depending upon operating conditions, and the pump can further be connected with any suitable power supply source (e.g., the main battery of the vehicle or any other battery).

Figure 7:
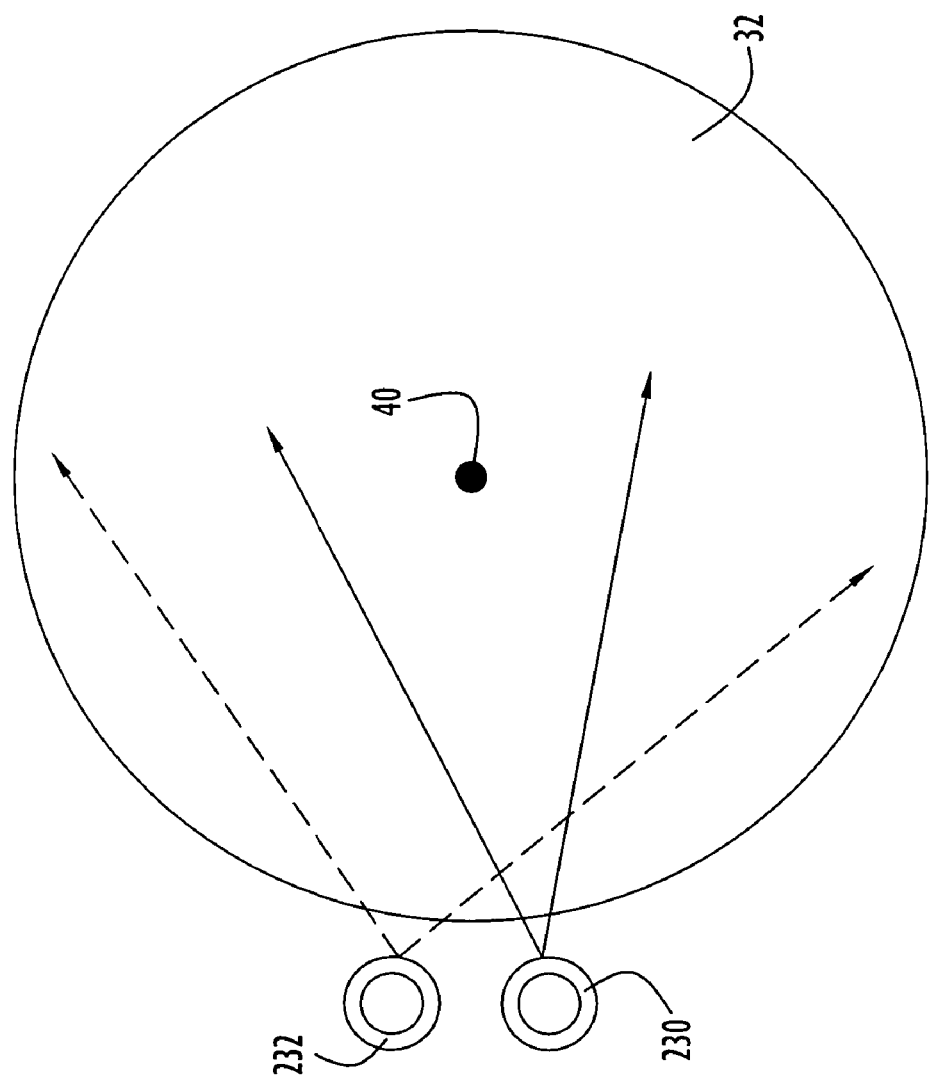
FIG. 7 is schematic view of the spray pattern for the spray nozzles of the system of FIG. 6.

Spray nozzles 230 and 232 are suitably aligned with respect to sensor window 32 to direct a spray of fluid from each nozzle toward the sensor window at different spray angles. Referring to FIG. 7, the spray nozzles are preferably stainless steel nozzles that deliver a flat spray at a selected coverage angle (e.g., about 60°). The spray nozzles are further designed and oriented in the system such that nozzle 230 delivers a fluid spray pattern toward sensor window 32 that includes and concentrates upon a central portion of the window, including the portion of the sensor window that is within the optical signal path (e.g., a laser signal path 40 as depicted in FIG. 7). Nozzle 232 delivers a fluid spray pattern that also includes the central portion but also washes across the sensor window and is slightly offset from the spray pattern generated by nozzle 230. While two spray nozzles are depicted in FIGS. 6 and 7, it is noted that any suitable number of spray nozzles (e.g., one or more) can be provided to spray a fluid in any suitable pattern or patterns and at coverage spray angles of any suitable sizes toward the sensor window.

In operation, pump 242 can be selectively actuated (e.g., by manipulation of the power switch by a system operator) to spray liquid from the nozzles toward sensor window 32 (e.g., when mud or other material becomes stuck on the window). The liquid spray effectively cleans the sensor window and removes any material that may not easily be removed from the airflow within the dog house gap. Upon removal of material from the sensor window, the liquid spray and material become entrained in the air flowing within the dog house gap and are removed from the dog house through tubular member 222.

As an alternative, or in combination with the fluid spray device, a gaseous spray device (e.g, an air knife) can be provided in close proximity to the sensor window to provide a jet of pressurized air or other gaseous fluid toward the sensor window to effect removal of material that may contact and stick to the window during operation of the sensor equipment.

The systems described above can be further modified such that the duct section withdraws air (or other gaseous fluids) from another source rather than the ambient environment surrounding the vehicle. For example, the duct section can be configured to withdraw air from a work space within any compartment or housing of the vehicle. Alternatively, a gaseous fluid such as nitrogen could be withdrawn from a storage tank or compartment and utilized to clean the sensor window and generate the desired pressure differential between the dog house and the surrounding ambient environment.

Thus, the dust mitigation and surface cleaning system of the invention can utilize a gaseous fluid flow (e.g., air, nitrogen, etc.) as described above, or a gaseous fluid flow in combination with liquid spray nozzles and/or gas jets to dislodge and remove any material that may become adhered to a surface as well as reduce or eliminate the presence of dust and/or other materials within a defined space that is adjacent or proximate the surface.

The dust mitigation and surface cleaning system of the invention is highly effective in systems employing optical sensor equipment in outdoor environments (e.g., in vehicles) or any other indoor or outdoor environments in which it is desirable or essential to maintain a surface (e.g., a lens or a window) substantially clean and free of dust and other materials during operation of the equipment.

It will be appreciated that the embodiments described above and illustrated in the drawings represent only a few of the many ways of implementing a dust mitigation and surface cleaning system in accordance with the present invention.

For example, the duct section can have any suitable size, shape and configuration and can further include any suitable number and types of filters and pressure generator devices (e.g., pumps, compressors and/or fans) to facilitate the filtering of air and delivery of the filtered air at any suitable pressure and flow rate into the dog house. The duct section can draw a gaseous fluid from an ambient environment surrounding the system and/or from some housing or internal environment within the system.

The dog house can have any suitable dimensions and configurations to at least partially surround a surface to be cleaned and to define a gap that receives air from the duct section for cleaning the surface. The tubular member of the dog house can have any suitable dimensions and configuration and can be disposed at any selected distance from the surface to be cleaned.

Any suitable number of nozzles and/or spray jets for spraying a liquid and/or gas toward the surface can be provided to supplement the cleaning by the air flow within the gap.

The dust mitigation and surface cleaning system is not limited to use in motorized vehicles. For example, the system can be implemented for use in maintaining a lens or sensor window clean for a fixed (and possible remote) optical equipment monitoring station (e.g., in a desert environment). Further, the system of the present invention is not limited to use with optical devices and/or outdoor applications. Rather, the system can be utilized with any device in which it is desired to maintain a surface of the device clean during operation of the device.

Having described preferred embodiments of a dust mitigation and surface cleaning system, variations and changes will be suggested to those skilled in the art in view of the teachings set forth herein. It is therefore to be understood that all such variations, modifications and changes are believed to fall within the scope of the present invention as defined by the appended claims.

What is claimed:

1. A dust mitigation and cleaning system for cleaning a surface, the system comprising:
   a system housing securable around at least a portion of a section including the surface to be cleaned, the system housing including a hollow member extending within the system housing toward and in general alignment with the surface to be cleaned, wherein an outlet of the system housing is defined by the hollow member, and the hollow member is completely separated from and does not contact the surface to be cleaned such that a gap exists between a terminal end of the hollow member and the surface to be cleaned;
   a duct section secured to a portion of the system housing and including an inlet to receive a gaseous fluid from a selected environment and an outlet in communication with the system housing; and
   a pressure generator disposed within the duct section;
   wherein operation of the pressure generator generates a pressure differential between an interior portion of the system housing and an ambient environment in which the system is disposed such that gaseous fluid drawn into the system housing via the duct section is removed from the interior portion of the system housing via the outlet defined by the hollow member.

2. The system of claim 1, wherein the duct section is configured to receive air from the ambient environment, and the pressure generator draws air from the ambient environment through the duct section and into the interior portion of the system housing.

3. The system of claim 1, further comprising:
   a filter disposed within the duct section to remove particulate material from the gaseous fluid drawn into the inlet of the duct section.

4. The system of claim 1, further comprising:
   a fluid supply device to inject a fluid directly upon the surface to be cleaned.

5. The system of claim 4, wherein the fluid supply device comprises at least one spray nozzle and a reservoir to supply liquid to the at least one spray nozzle to facilitate spraying of the surface to be cleaned with the liquid.

6. The system of claim 1, wherein a distance defined by the gap between the terminal end of the hollow member and the surface is no greater than about 5 centimeters.

7. The system of claim 1, wherein the system is mountable to a motorized vehicle, the system housing is configured to be secured around at least a portion of a housing structure that contains optical sensor equipment, and the surface to be cleaned comprises a sensor window defining a wall portion of the housing structure.

8. The system of claim 7, wherein the system housing is securable to a lower surface of the motorized vehicle so as to align and define an optical path between the sensor window with the hollow member to permit an optical signal to travel between the optical sensor equipment and a ground surface upon which the motorized vehicle is supported.

9. The system of claim 7, wherein the system housing completely surrounds and contains the housing structure that contains optical sensor equipment.

10. A monitoring system comprising:
    an equipment housing including optical sensor equipment and a sensor window through which an optical signal is transmitted and processed; and
    a dust mitigation and cleaning system to maintain the sensor window clean, the dust mitigation and cleaning system comprising:
    a system housing secured around at least a portion of the equipment housing that includes the sensor window, the system housing including a hollow member extending within the system housing toward and in general alignment with the sensor window, wherein an outlet of the system housing is defined by the hollow member, the hollow member is completely separated from and does not contact the surface to be cleaned such that a gap exists between a terminal end of the hollow member and the surface to be cleaned, and an optical path for transmitting the optical signal from the optical sensor equipment to an ambient environment surrounding the monitoring system is defined between the sensor window and the hollow member;
    a duct section secured to a portion of the system housing and including an inlet to receive a gaseous fluid from a selected environment and an outlet in communication with the system housing; and
    a pressure generator disposed within the duct section;
    wherein operation of the pressure generator generates a pressure differential between an interior portion of the system housing and the ambient environment such that gaseous fluid drawn into the system housing via the duct section is removed from the interior portion of the system housing via the outlet defined by the hollow member.

11. The system of claim 10, wherein the duct section is configured to receive air from the ambient environment, and the pressure generator draws air from the ambient environment through the duct section and into the interior portion of the system housing.

12. The system of claim 10, wherein the optical sensor equipment transmits a laser signal to the ambient environment via the optical path.

13. The system of claim 10, further comprising:
a filter disposed within the duct section to remove particulate material from the gaseous fluid drawn into the inlet of the duct section.

14. The system of claim 10, further comprising:
a fluid supply device to inject a fluid directly upon the sensor window.

15. The system of claim 14, wherein the fluid supply device comprises at least one spray nozzle and a reservoir to supply liquid to the at least one spray nozzle to facilitate spraying of the sensor window with the liquid.

16. The system of claim 10, wherein a distance defined by the gap between the terminal end of the hollow member and the surface is no greater than about 5 centimeters.

17. The system of claim 10, further comprising:
a motorized vehicle;
wherein the system housing is secured to a lower surface of the motorized vehicle, a first portion of the equipment housing is secured within the motorized vehicle and a second portion of the equipment housing extends through the motorized vehicle and within the system housing, and the hollow member and the sensor window are aligned with the motorized vehicle such that an optical signal is transmitted through the optical path toward a ground surface upon which the motorized vehicle is supported.

18. The system of claim 10, wherein the system housing completely surrounds and contains the equipment housing.

19. A method of maintaining a surface clean with a dust mitigation and surface cleaning system, the method comprising:
providing a system housing that is secured around at least a portion of a section including the surface to be cleaned;
drawing a gasous fluid, via a pressure generator, from a selected environment and into a duct section;
facilitating a flow of the gasous fluid from the duct section into an interior portion of the system housing; and
providing a hollow member within the system housing that extends toward and is in general alignment with the surface to be cleaned, wherein the hollow member defines an outlet of the system housing that facilitates removal of gaseous fluid drawn into the system housing via the duct section from the interior portion of the system housing and to an ambient environment surrounding the system;
wherein the hollow member is completely separated from and does not contact the surface to be cleaned such that a gap exists between a terminal end of the hollow member and the surface to be cleaned and a gaseous fluid flowing within the interior portion of the system housing contacts and cleans the surface prior to removal of the gaseous fluid from the system housing.

20. The method of claim 19, wherein the pressure generator draws air from the ambient environment surrounding the system through the duct section and into the interior portion of the system housing.

21. The method of claim 19, further comprising:
filtering the gaseous in the duct section, via a filter, prior to the gaseous being provided to the system housing.

22. The method of claim 19, further comprising:
injecting a fluid from a fluid supply device directly upon the surface.

23. The method of claim 22, wherein the fluid supply device comprises at least one spray nozzle and a reservoir to supply liquid to the at least one spray nozzle, and the at least one spray nozzle sprays liquid directly upon the surface.

24. The method of claim 19, wherein a distance defined by the gap between the terminal end of the hollow member and the surface is no greater than about 5 centimeters.

25. The method of claim 19, wherein the surface to be cleaned comprises a sensor window secured to an equipment housing, the equipment housing includes sensor equipment, and at least a portion of the equipment housing is secured within the system housing, the method further comprising:
transmitting an optical signal from the sensor equipment through the sensor window and the hollow member aligned with the sensor window and to the ambient environment surrounding the system.

26. The method of claim 25, wherein the optical signal comprises a laser signal.

27. The method of claim 25, wherein the system housing and equipment housing are secured to a motorized vehicle, and the optical signal is further transmitted from the motorized vehicle to the ambient environment surrounding the motorized vehicle.

28. The method of claim of claim 27, wherein the system housing and equipment housing are aligned with respect to the motorized vehicle such that the optical signal is transmitted toward a ground surface upon which the motorized vehicle is supported.

* * * * *